US008226624B2

(12) United States Patent
Hancock-Cooke et al.

(10) Patent No.: US 8,226,624 B2
(45) Date of Patent: Jul. 24, 2012

(54) ELASTIC MEMBER FOR A GARMENT HAVING IMPROVED GASKETING

(75) Inventors: Catherine Marguerite Hancock-Cooke, Neenah, WI (US); Sara Jane Wille Stabelfeldt, Appleton, WI (US); Janis Wilson Hughes, Apharetta, GA (US); Wing-Chak Ng, Suwanee, GA (US); Debra Jean McDowall, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 352 days.

(21) Appl. No.: 11/848,594

(22) Filed: Aug. 31, 2007

(65) Prior Publication Data

US 2009/0062763 A1 Mar. 5, 2009

(51) Int. Cl.
*A61F 13/15* (2006.01)
*A61F 13/20* (2006.01)

(52) U.S. Cl. ........... 604/385.03; 604/385.24; 604/385.3; 604/385.22; 604/385.01

(58) Field of Classification Search ............. 604/385.03, 604/385.24, 385.3
See application file for complete search history.

(56) References Cited

U.S. PATENT DOCUMENTS

| | | | |
|---|---|---|---|
| 3,338,992 A | | 3/1886 | Loomis |
| 2,931,361 A | * | 4/1960 | Sostrin ......................... 604/392 |
| 3,341,394 A | | 9/1967 | Kinney |
| 3,502,763 A | | 3/1970 | Hartmann |
| 3,542,615 A | | 11/1970 | Dobo et al. |
| 3,692,618 A | | 9/1972 | Dorschner et al. |
| 3,705,070 A | * | 12/1972 | Kim ............................... 428/112 |
| 3,802,817 A | | 4/1974 | Matsuki et al. |
| 3,849,241 A | | 11/1974 | Butin et al. |
| 4,036,233 A | * | 7/1977 | Kozak .......................... 604/370 |
| 4,063,559 A | * | 12/1977 | Tritsch ......................... 604/390 |
| 4,323,534 A | | 4/1982 | DesMarais |
| 4,340,563 A | | 7/1982 | Appel et al. |
| 4,500,316 A | * | 2/1985 | Damico ........................ 604/389 |
| 4,597,760 A | * | 7/1986 | Buell ............................ 604/397 |
| 4,655,760 A | | 4/1987 | Morman et al. |

(Continued)

FOREIGN PATENT DOCUMENTS

EP 0150714 A2 10/1988

(Continued)

OTHER PUBLICATIONS

English Abstract of JP 10337300, Published Dec. 22, 1998.

(Continued)

*Primary Examiner* — Tatyana Zalukaeva
*Assistant Examiner* — Susan Su
(74) *Attorney, Agent, or Firm* — Dority & Manning, P.A.

(57) ABSTRACT

Various garments are disclosed which include a body adhesive for attaching the garment to the skin of a wearer. More particularly, the garment can include at least one extensible portion. An adhesive member comprising an adhesive layer and a cover member may be positioned over the extensible portion. The cover member may completely cover the adhesive layer when the extensible portion is in a relaxed condition. When the extensible portion is stretched, however, the cover member may define openings that expose the adhesive layer for adhering the adhesive to a wearer. The garment may comprise, for instance, a diaper, a training pant, a swim pant, a hospital gown, an industrial garment, a glove, a feminine hygiene product, an adult incontinence product, and the like. The adhesive member can be positioned over any suitable extensible portion on the garment.

23 Claims, 7 Drawing Sheets

U.S. PATENT DOCUMENTS

| | | | |
|---|---|---|---|
| 4,657,802 A | 4/1987 | Morman | |
| 4,663,220 A | 5/1987 | Wisneski et al. | |
| 4,704,116 A | 11/1987 | Enloe | |
| 4,707,398 A | 11/1987 | Boggs | |
| 4,720,415 A | 1/1988 | Vander Wielen et al. | |
| 4,724,184 A | 2/1988 | Killian et al. | |
| 4,741,949 A | 5/1988 | Morman et al. | |
| 4,753,648 A * | 6/1988 | Jackson | 604/389 |
| 4,781,966 A | 12/1988 | Ballweg | |
| 4,789,699 A | 12/1988 | Kieffer et al. | |
| 4,795,456 A * | 1/1989 | Borgers et al. | 604/390 |
| 4,820,572 A | 4/1989 | Killian et al. | |
| 4,834,738 A | 5/1989 | Klelpikowski et al. | |
| 4,846,825 A * | 7/1989 | Enloe et al. | 604/385.22 |
| 4,923,742 A | 5/1990 | Killian et al. | |
| 4,940,464 A | 7/1990 | Van Gompel et al. | |
| 4,965,122 A | 10/1990 | Morman | |
| 4,981,747 A | 1/1991 | Morman | |
| 5,093,422 A | 3/1992 | Himes | |
| 5,114,781 A | 5/1992 | Morman | |
| 5,116,662 A | 5/1992 | Morman | |
| 5,226,992 A | 7/1993 | Morman | |
| 5,304,599 A | 4/1994 | Himes | |
| 5,332,613 A | 7/1994 | Taylor et al. | |
| 5,336,545 A | 8/1994 | Morman | |
| 5,486,166 A | 1/1996 | Bishop et al. | |
| 5,490,846 A | 2/1996 | Ellis et al. | |
| 5,575,783 A * | 11/1996 | Clear et al. | 604/385.22 |
| 5,618,281 A * | 4/1997 | Betrabet et al. | 604/387 |
| 5,733,275 A * | 3/1998 | Davis et al. | 604/387 |
| 5,766,389 A | 6/1998 | Brandon et al. | |
| 5,804,021 A * | 9/1998 | Abuto et al. | 156/252 |
| 5,807,367 A * | 9/1998 | Dilnik et al. | 604/369 |
| 5,820,973 A | 10/1998 | Dodge, II et al. | |
| 5,827,259 A | 10/1998 | Laux et al. | |
| 5,873,868 A * | 2/1999 | Nakahata | 604/383 |
| 6,135,988 A * | 10/2000 | Turner et al. | 604/387 |
| 6,258,076 B1 | 7/2001 | Glaug | |
| 6,262,331 B1 * | 7/2001 | Nakahata et al. | 604/383 |
| 6,277,106 B1 * | 8/2001 | Boudry et al. | 604/394 |
| 6,461,715 B1 * | 10/2002 | Guenther et al. | 428/131 |
| 6,478,784 B1 * | 11/2002 | Johnson et al. | 604/385.01 |
| 6,491,677 B1 * | 12/2002 | Glaug et al. | 604/387 |
| 6,620,143 B1 * | 9/2003 | Zacharias et al. | 604/385.03 |
| 6,626,879 B1 * | 9/2003 | Ashton et al. | 604/385.03 |
| 6,645,190 B1 | 11/2003 | Olson et al. | |
| 6,647,549 B2 | 11/2003 | McDevitt | |
| 6,710,099 B2 | 3/2004 | Cinelli et al. | |
| 6,746,433 B1 * | 6/2004 | Shimoe et al. | 604/385.01 |
| 2003/0199841 A1 * | 10/2003 | Ashton et al. | 604/385.01 |
| 2004/0122404 A1 * | 6/2004 | Meyer et al. | 604/385.19 |
| 2004/0122411 A1 * | 6/2004 | Hancock-Cooke | 604/385.29 |
| 2004/0147890 A1 * | 7/2004 | Nakahata et al. | 604/385.01 |
| 2006/0247591 A1 * | 11/2006 | Hughes et al. | 604/383 |
| 2007/0030740 A1 | 2/2007 | Wada et al. | |

FOREIGN PATENT DOCUMENTS

| | | |
|---|---|---|
| EP | 0312071 A2 | 4/1989 |
| EP | 0850625 A1 | 7/1998 |
| EP | 1194097 A1 | 4/2002 |
| EP | 0873739 A1 | 4/2004 |
| EP | 1707171 A2 | 10/2006 |
| WO | WO 0037008 A1 | 6/2000 |
| WO | WO 0037009 A2 | 6/2000 |

OTHER PUBLICATIONS

English Abstract of KR 100163509, Published Sep. 7, 1998.
International Search Report, PCT/IB2008/052560, Published Jan. 5, 2009.

* cited by examiner

ELASTIC MEMBER FOR A GARMENT HAVING IMPROVED GASKETING

BACKGROUND

Many disposable garments, such as diapers, incontinence articles, training pants, feminine hygiene products, hospital gowns, bandages, and the like include various elastic portions that are intended to give the garments form fitting properties. For example, many disposable diapers include elastic members positioned around the waist of the garment and leg elastics which are intended to surround the legs of the wearer. In addition, diapers can also include elasticized, longitudinally extending barrier flaps which encircle the upper thighs of the wearer. The above elastic portions are intended to not only make the garment more comfortable to wear, but are also used to inhibit the leakage of body fluids from the absorbent article.

In addition to elastic portions, in the past, those skilled in the art have also proposed placing adhesives on garments whereby the adhesive may engage the skin of the wearer when the garment is being worn. The adhesive may be positioned on the garment, for instance, to further inhibit the leakage of body exudates from the absorbent article or inhibit the leakage of other fluids. For example, the use of adhesives on absorbent articles is disclosed in PCT Application Publication Number WO 97/17926 (U.S. Pat. No. 6,277,106) and in PCT Application Publication Number WO 00/37008 (U.S. Pat. No. 6,135,988), which are both incorporated herein by reference.

Although the use of adhesives for securing garments to the wearer's skin has shown to be effective in preventing the leakage of fluids from the garments, problems have been experienced in finding a mechanism that delivers the adhesive on the garment for later attachment to the wearer. For example, in the past, the adhesive areas have been covered with a peelable strip that the user is to remove prior to donning the garment. Consumers, however, have been reluctant to expose the adhesive and thus, in some situations, have opted not to remove the peel strip. Some users, for instance, have a tendency to believe that the exposed adhesive will somehow create a certain amount of discomfort for the wearer instead of improving fit and performance.

In view of the above, a need currently exists for an improved construction for incorporating body adhesives into garments. For instance, a need exists for a garment that incorporates adhesives that automatically adhere to the wearer's skin when the garment is donned.

SUMMARY

In general, the present disclosure is directed to various garments that include at least one adhesive member that adheres the garment to a wearer's skin through the use of a body adhesive. In accordance with the present disclosure, an adhesive layer is positioned over an extensible portion of the garment. When the extensible member is in an unstretched condition, the adhesive remains covered and thus not exposed. When the extensible member is stretched, however, the adhesive member is designed to expose the adhesive for attachment to the wearer's skin. In one embodiment, the adhesive member can be constructed so that only a certain amount of adhesive is exposed and contacted with the wearer's skin when the garment is donned. In this manner, not only does the adhesive become automatically exposed when the garment is worn, but the adhesive does not substantially interfere with the comfort of the garment. In one embodiment, the extensible member can be elastic.

In one embodiment, for instance, the present disclosure is directed to a garment comprising a chassis having a shape configured to surround a portion of a wearer's body. The chassis includes an outer surface and an inner surface that is placed adjacent to the wearer's body. The garment includes an extensible portion that permits the chassis to expand in a particular area for providing the chassis with a form fitting property around a portion of a wearer's body. Additionally, the extensible portion can also be elastic to provide additional form fitting characteristics. In accordance with the present disclosure, an adhesive member is positioned on the inner surface of the chassis and over the extensible portion. The adhesive member includes an adhesive layer and a cover member. The cover member substantially covers the adhesive layer. When the adhesive member is stretched with the extensible portion, however, the cover member defines openings that expose the adhesive layer for adhering the adhesive member to a wearer's skin.

In one embodiment, for example, the garment may comprise an absorbent article, such as a diaper, training pants, a feminine hygiene product, or an adult incontinence product. The absorbent article may include an outer cover, a liner, and an absorbent core positioned in between the outer cover and the liner. The adhesive member may be positioned on the inner surface of the liner over an extensible portion. The extensible portion, for instance, may comprise a waist elastic member or a leg elastic member.

In an alternative embodiment, the garment may comprise a hospital gown or the like. The extensible portion, for instance, may form a cuff on the garment that is intended to surround the wearer's arm or leg. The adhesive member may be positioned on the cuff in order to provide a better fit.

The extensible portion contained within the garment can be made from any suitable extensible material. In one embodiment, for instance, the extensible portion can be elastic and comprise an elastic film, an elastic woven material, or an elastic nonwoven material. In one embodiment, the elastic portion may comprise an elastic laminate, such as a stretch bonded laminate. The adhesive layer of the adhesive member can be applied directly to the elastic portion.

The cover material positioned over the adhesive layer can also comprise any suitable material. For instance, the cover member may comprise a woven material, a nonwoven material, or a film. In one embodiment, for instance, the cover member may comprise a spunbond web.

In order for the cover member to define the openings, in one embodiment, the cover member may include a plurality of apertures, such as slits, that form the openings when the cover member is stretched. The slits, for instance, may extend in a direction that is generally perpendicular to the direction in which the extensible portion is stretched while being worn. In one embodiment, the slits have a length that is from about 10 percent to about 80 percent of the length of the cover member, such as from about 50 percent to about 70 percent of the length of the cover member. In one embodiment, for instance, the slits can have a length from about 3 mm to about 12 mm.

As described above, the cover member may include a plurality of slits. In one embodiment, the slits can be positioned generally parallel to each other. The space between the slits can vary depending upon the particular application. In one embodiment, for instance, the slits can be from about 3 mm to about 10 mm apart. Additionally, the slits can be parallel and offset to adjacent slits. In another embodiment, there may a plurality of vertically extending strips defining a column of slits. Each column of multiple slits may be defined offset to adjacent columns of multiple slits.

In addition to slits, the cover member may define a plurality of apertures. The cover member, for instance, may comprise a gathered layer that, when stretched, exposes the apertures.

The amount of surface area that is exposed when the cover member is stretched can also depend upon various factors. In one embodiment, for instance, the exposed surface area may be from about 0.01 square cm to about 10 square cm, such as from about 0.05 square cm to about 5 square cm.

The adhesive used to form the adhesive layer is generally an adhesive that has relatively low tack. The adhesive, for instance, should attach to one's skin while also being readily removable. The adhesive may comprise, for instance, a silicone, an acrylic, a polyurethane, a polyester, a polyamide, a styrene butadiene, a polyisobutylene, a polybuadiene, a polyisoprene, a polyvinyl alcohol, a polyvinyl acetate, a methyl cellulose, a styrene-butadiene-styrene, a styrene-isoprene-styrene, a styrene-ethylenepropylene-styrene, a styrene-ethylenepropylene-styrene-ethylenepropylene, a styrene-ethylene butylene-styrene, and mixtures thereof.

The adhesive layer, for instance, may have a peel strength of no more than about 240 grams per centimeter. The adhesive may have a shear storage modulus of from about $1.0 \times 10^3$ to about $6.0 \times 10^6$ dynes per square centimeter as measured at a temperature of 20° C. and at a frequency of 10 radians per second. The adhesive may also have an initial shear strength of no more than about 600 grams per square cm. In addition, the adhesive may be configured to provide an aged shear strength of no more than about 600 grams per square centimeter and may provide a cyclic shear value of no more than about 100 cycles.

The adhesive layer contained below the cover member may comprise a continuous layer or discontinuous layer. When discontinuous, for instance, the adhesive may only be positioned below each of the openings defined in the cover member.

Other features and aspects of the present disclosure are discussed in greater detail below.

BRIEF DESCRIPTION OF THE DRAWINGS

A full and enabling disclosure of the present disclosure, including the best mode thereof to one skilled in the art, is set forth more particularly in the remainder of the specification, including reference to the accompanying Figures, in which.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to an improved construction for incorporating body adhesives into garments. The garments constructed in accordance with the present disclosure can comprise, for instance, disposable articles, such as diapers, training pants, swim pants, feminine hygiene products, adult incontinence products, surgical drapes, hospital and industrial gowns and clothing, bandages, and the like. The adhesive applied to the garment is intended to adhere the garment directly to the user's skin and can provide numerous benefits and advantages.

For example, when used on an absorbent article such as a diaper, the adhesive can be used provide an effective seal so as to prevent the leakage of any body fluids from the absorbent article. When applied to other garments, however, the adhesive may also be used to prevent contaminants such as airborne particulate matter or fluids from entering the garment. In general, the use of such adhesives has not been favored by consumers in the past. The present disclosure is directed an improved method of incorporating the adhesive into the garment and of adhering the adhesive to a user's skin so as to minimize any discomfort that may be associated with the use of the adhesive.

As will be explained in greater detail below, in accordance with the present disclosure, an adhesive layer is placed over an extensible portion in a garment facing towards the wearer. A cover layer covers the adhesive layer so that when the extensible portion is in a relaxed condition, the adhesive remains covered and not exposed. When the extensible portion is stretched, however, the cover member creates openings that expose the adhesive for attachment to a wearer's body. The adhesive strength of the adhesive and the number and size of the openings created by the cover member can be carefully controlled, if desired, so that only a certain amount of adhesive at a particular strength is contacted with the skin of the user. Through the above construction, an adhesive is incorporated into the garment that does not become exposed until the garment is donned. Further, the amount of exposure can be controlled so as to minimize any discomfort associated with the adhesive.

Figure 1:
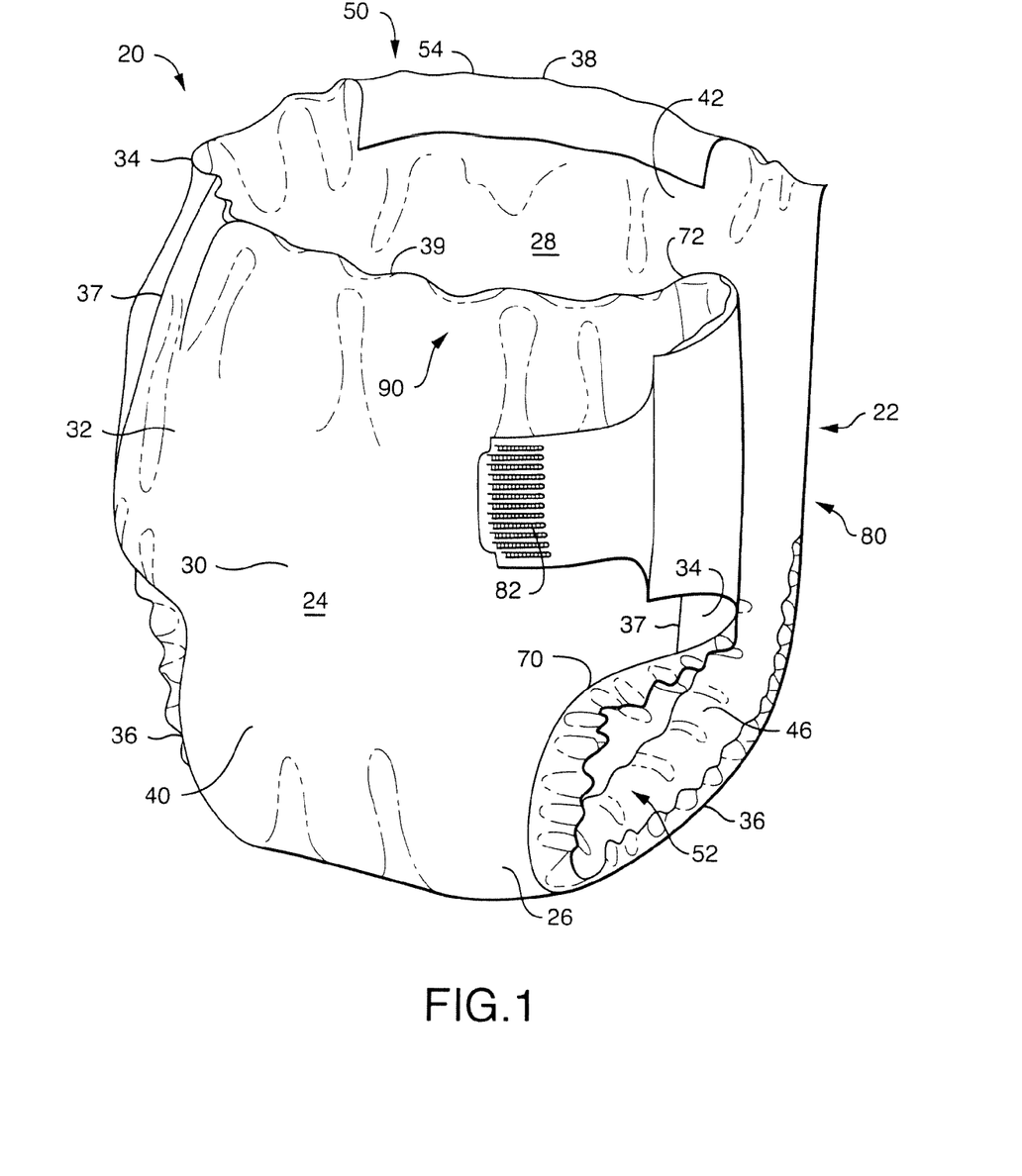
FIG. 1 is a rear perspective view of one embodiment of a garment made in accordance with the present disclosure.
Figure 2:
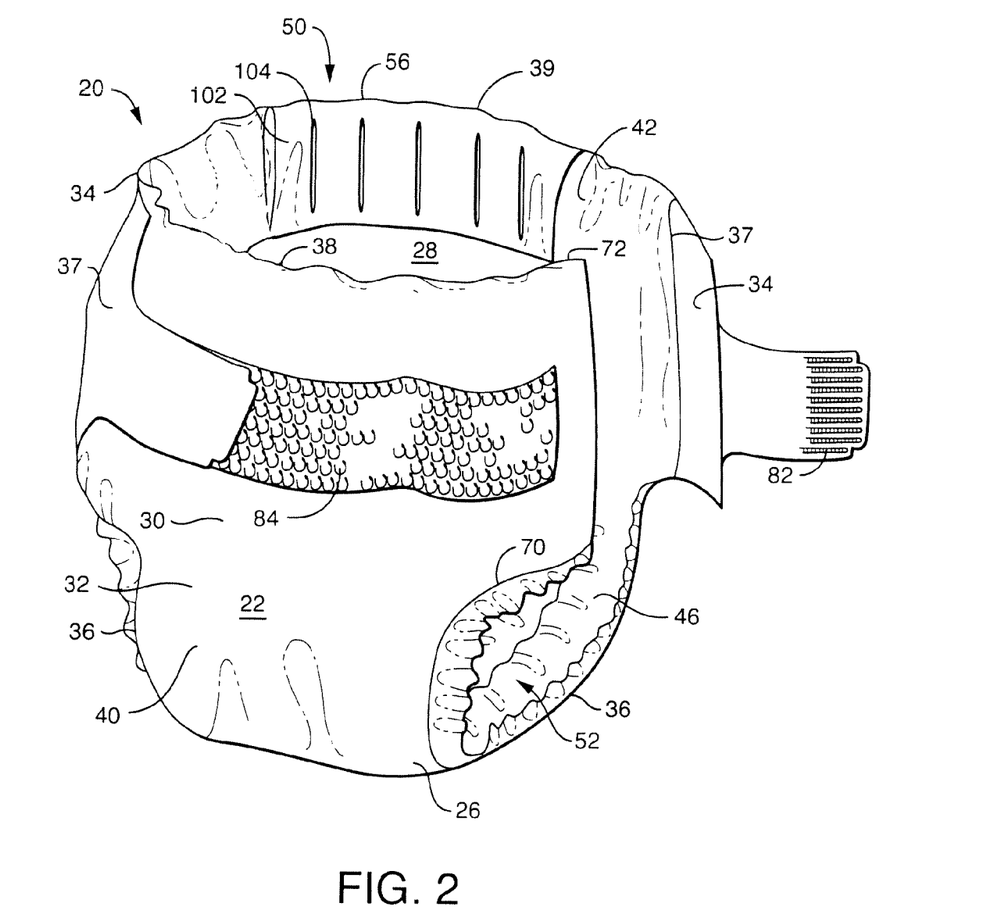
FIG. 2 is a front perspective view of the garment illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other garments intended for personal wear, including but not limited to diapers, training pants, swim pants, feminine hygiene products, incontinence products, medical garments, gloves, surgical pads and bandages, other personal care, health care or industrial garments, and the like without departing from the scope of the present disclosure.

By way of illustration only, various materials and methods for constructing absorbent articles such as the diaper 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
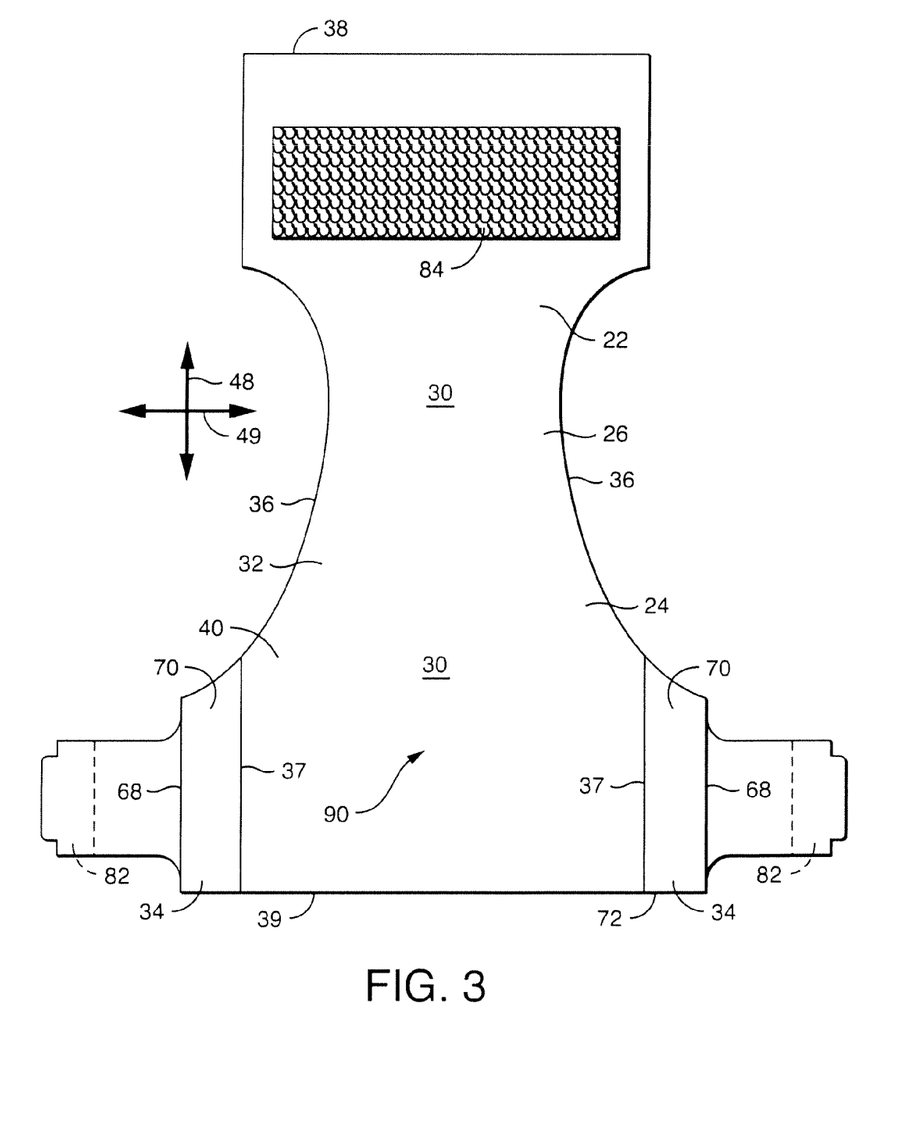
FIG. 3 is a plan view of the garment shown in FIG. 1 with the article in an unfastened, unfolded and laid flat condition showing the surface of the article that faces away from the wearer.
Figure 4:
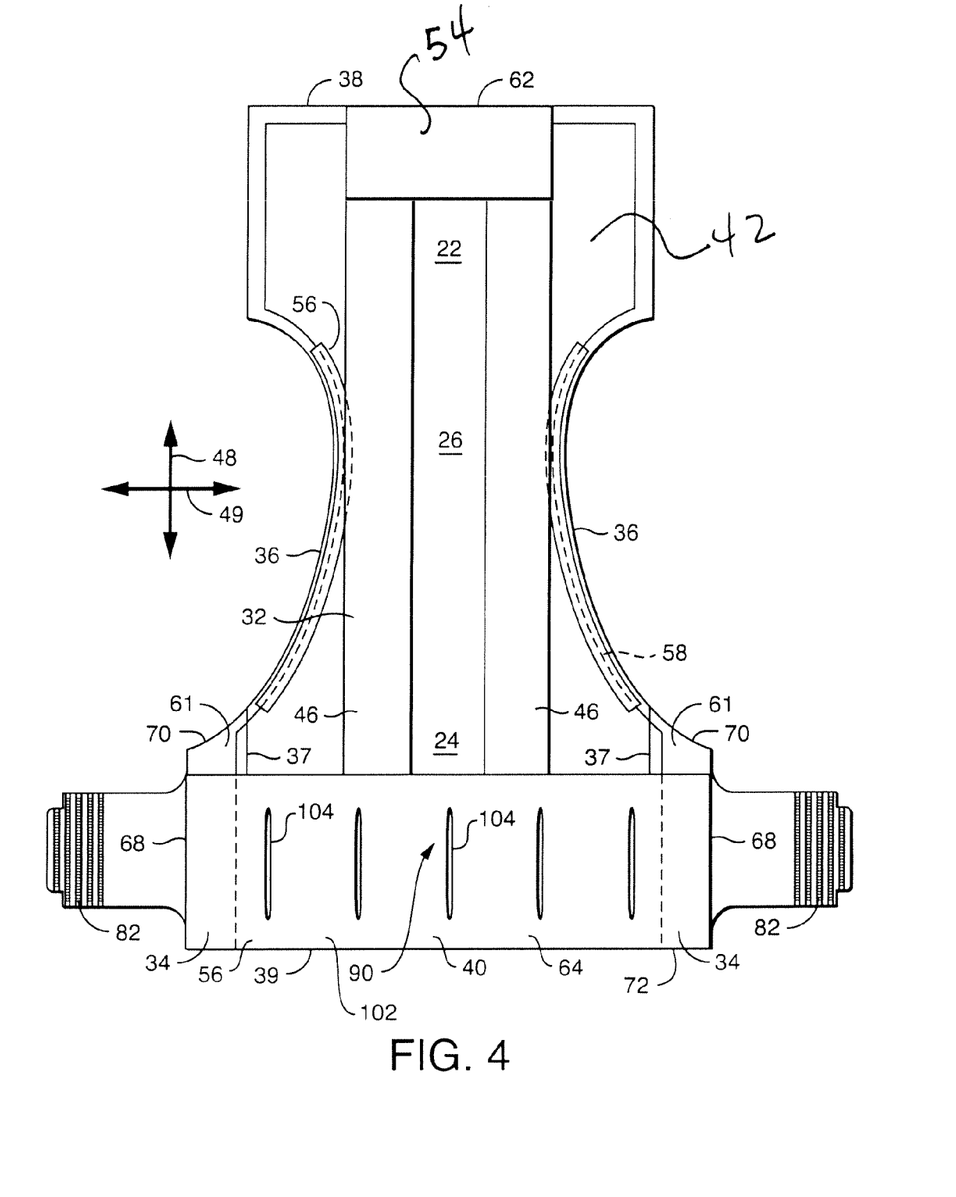
FIG. 4 is a plan view similar to FIG. 3 showing the surface of the garment that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure (not shown) disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

Figure 9:
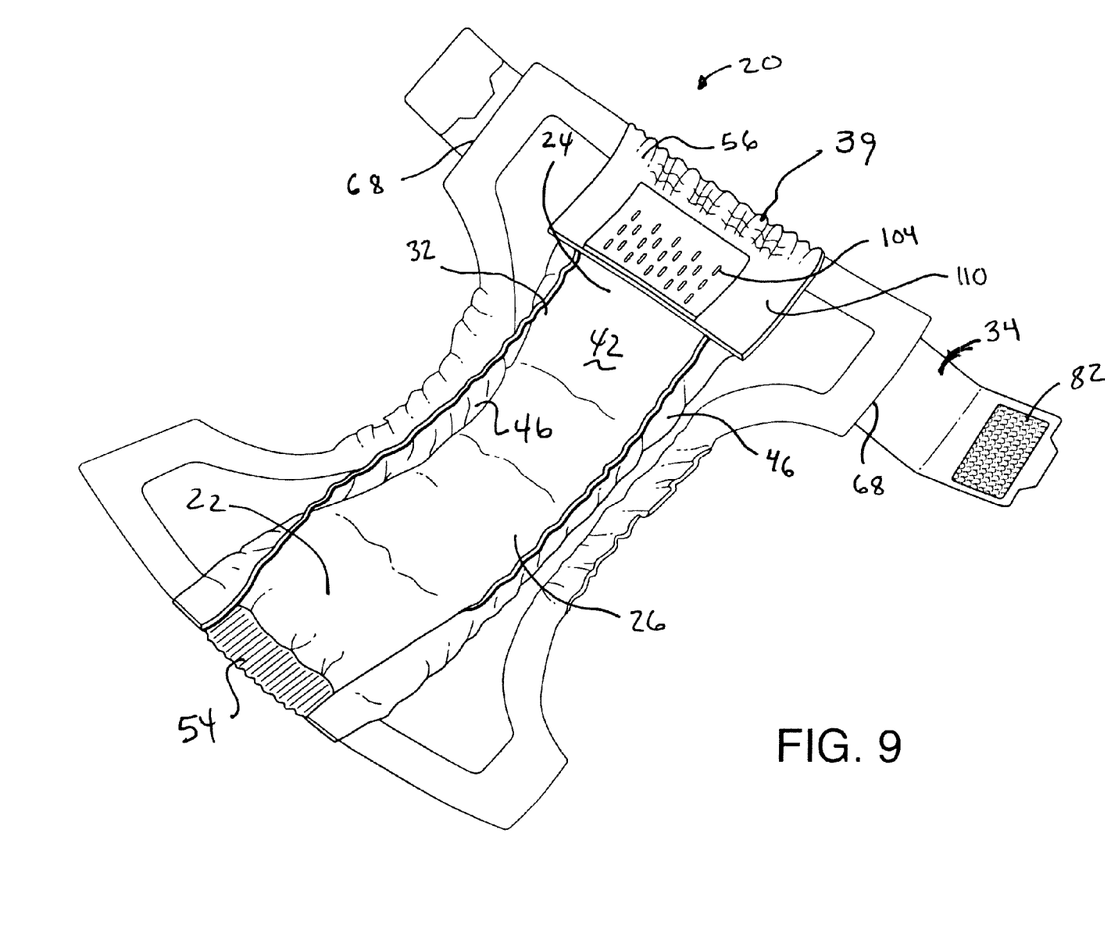
FIG. 9 is a perspective view of another embodiment of a garment made according to the present disclosure.

The elasticized containment flaps 46 as shown in FIG. 4 define a partially unattached edge which assumes an upright configuration in at least the crotch region 26 of the diaper 20 to form a seal against the wearer's body (see also FIG. 9). The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

In some embodiments, the absorbent article 20 may further include a surge management layer (not shown) which may be optionally located adjacent the absorbent structure (not shown) and attached to various components in the article 20 such as the absorbent structure (not shown) or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the Figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

As shown, the absorbent article 20 may include various extensible waist members. These extensible waist members may also be elastic for providing elasticity around the waist opening. For example, as shown in FIG. 4, the absorbent article 20 can include a front waist elastic member 54 and/or a back waist elastic member 56. The waist elastic members 54 and 56 are for providing the absorbent article with at least one form fitting property. The waist elastic members also prevent leakage of body fluids from the absorbent article.

In the embodiment illustrated in the figures, the extensible members face the inside of the absorbent article and are attached to the inside surface of the chassis. In one embodiment, the entire perimeter of the extensible members may be secured to the chassis. In other embodiments, however, only the top edge or the bottom edge of the extensible member is secured to the chassis.

For example, referring to FIG. 9, an alternative embodiment of an absorbent article 20 made in accordance with the present disclosure is illustrated. Like reference numerals have been used to indicate similar elements. As shown, in this embodiment, the waist elastic member 56 is attached to the absorbent article generally along one end of the elastic member. For example, as shown, the waist elastic member 56 is joined to the absorbent article along the waist edge 39. In this manner, the waist elastic member 56 forms a flap 110 that can be secured to a user in accordance with the present disclosure. When secured to a user, for instance, the flap 110 is well suited to containing body fluids including fecal matter within the absorbent article. The manner in which the flap is secured to a wearer is described in greater detail below with reference to FIGS. 5-8.

In still another embodiment, the entire chassis may be made from an extensible material. In this embodiment, for instance, the entire chassis may be considered an extensible member. For example, in one embodiment, the entire chassis can be made from an elastic member that stretches and contracts.

In order for the extensible member to have elastic properties, the extensible member includes at least one elastomeric component. In general, any material known in the art to possess elastomeric characteristics can be used in the present disclosure as an elastomeric component. Useful elastomeric materials can include, but are not limited to, films, strands, foams, nonwoven materials, etc. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers for the A and A' blocks, and the present block copolymers are intended to embrace linear, branched and radial block copolymers. The elastomeric nonwoven web may be formed from, for example, elastomeric (polystyrene/poly(ethylene-butylene)/polystyrene) block copolymers. Commercial examples of such elastomeric copolymers are, for example, those known as KRATON® materials which are available from Kraton Polymers, LLC of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A-B-A-B tetrablock copolymer may also be used. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Kraton Polymers, LLC of Houston, Tex. under the trade designation KRATON® G-1657.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Arnhem, Holland and now available from DSM of Sittard, Holland.

Another suitable material is a polyester block amide copolymer. Such materials are available in various grades under the trade designation PEBAX® from ELF Atochem Inc. of Glen Rock, N.J. Examples of the use of such polymers may be found in U.S. Pat. Nos. 4,724,184, 4,820,572 and 4,923,742 to Killian.

Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

Thermoplastic copolyester elastomers may also be used. Commercial examples of such copolyester materials are, for example, those known as ARNITEL®, formerly available from Akzo Plastics of Amhem, Holland and now available from DSM of Sittard, Holland, or those known as HYTREL® which are available from E.I. DuPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs.

Elastomeric olefin polymers are available from Exxon Chemical Company of Baytown, Tex. under the trade name ACHIEVE® for polypropylene based polymers and EXACT® and EXCEED® for polyethylene based polymers. Dow Chemical Company of Midland, Mich. has polymers commercially available under the name ENGAGE®. These materials are believed to be produced using non-stereoselective metallocene catalysts. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites.

When incorporating an elastomeric component, such as described above, into an extensible member of the present disclosure, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

In one embodiment, the elastic member can be a neck stretched bonded laminate. As used herein, a neck stretched bonded laminate is defined as a laminate made from the combination of a neck bonded laminate and a stretch bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction.

In one particular embodiment, the elastic member comprises a stretch-bonded laminate. The stretch-bonded laminate can include elastic threads made from an elastomeric material sandwiched between two polypropylene spunbond layers. The elastic threads can be, for instance, made from a styrene-ethylene butylene-styrene block of polymer, such as KRATON G2740, available from Krayton Polymers, LLC. The stretch-bonded laminate, for instance, can have a basis weight of from about 0.5 osy to about 8 osy, and particularly from about 1.5 osy to about 3.5 osy.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

In accordance with the present disclosure, an adhesive member is placed over the extensible member on the absorbent article, such as over the front waist elastic member 54 and/or over the back waist elastic member 56. The adhesive member generally comprises an adhesive layer positioned below a cover member. When the extensible member is in a relaxed condition, the cover member substantially covers the adhesive layer such that substantially no adhesive is exposed. When the extensible member is stretched, however, the cover member is configured to create openings that expose the adhesive for attachment to the skin of a wearer. Thus, in accordance to the present disclosure, the adhesive member is constructed such that the adhesive automatically becomes exposed when the absorbent article is donned by a wearer.

Figure 5:
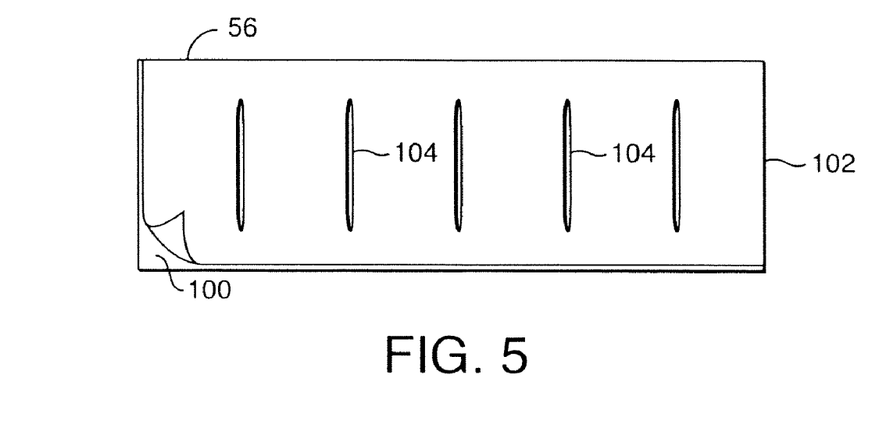
FIG. 5 is a plan view of one embodiment of an extensible adhesive member made in accordance with the present disclosure.
Figure 6:
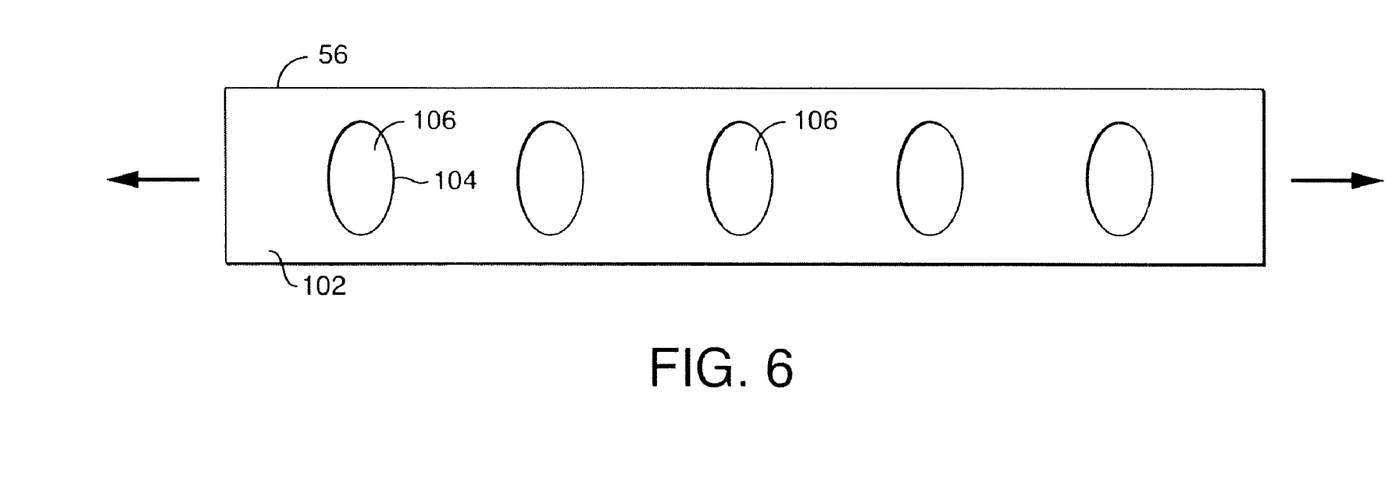
FIG. 6 is a plan view of the extensible adhesive member shown in FIG. 5 illustrated in a stretched condition.

Referring to FIGS. 5 and 6, one embodiment of the back waist elastic member 56 is shown in greater detail illustrating an adhesive member made in accordance with the present disclosure. As shown, an adhesive layer 100 has been applied to the outer surface of the elastic member 56. In addition, a cover member 102 is shown positioned over the adhesive layer 100. In accordance with the present disclosure, the cover member 102 defines a plurality of slits or apertures 104.

Although the slits can have any suitable orientation, in the embodiment shown, the slits 104 are positioned generally perpendicular to the direction in which the elastic member 56 is stretched during wear. More particularly, the slits 104 are generally perpendicular to the lateral direction of the elastic member. In other embodiments, however, the slits 104 may generally be positioned at a diagonal to the lateral direction.

The slits 104, as shown, can generally be spaced along the cover member 102 and can be generally positioned parallel to one another. The slits 104 generally do not extend over the entire length of the cover member 102 so that the cover member 102 does not break into multiple pieces when the elastic member 56 is stretched. The slits 104, for instance, can have a length that is from about 10 percent to about 80 percent of the length of the cover member 102. For instance, in one embodiment, the slits 104 can have a length that is about 50 percent to about 70 percent of the length of the cover member.

Figure 7:
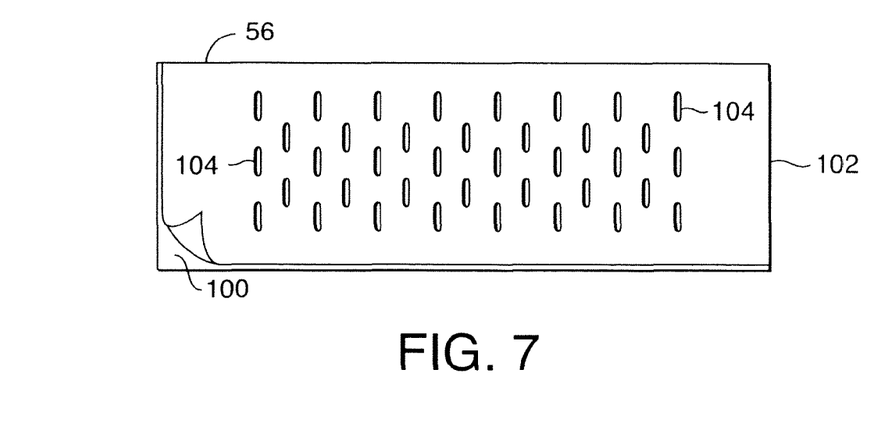
FIG. 7 is a plan view of another embodiment of an extensible adhesive member made in accordance with the present disclosure.

Referring to FIGS. 6 and 7, another embodiment of a back waist elastic member made in accordance with the present disclosure is shown. Like reference numerals have been used to indicate similar elements. As shown, in this embodiment, the elastic member 56 is coated with an adhesive layer 100. A cover member 102 defining a plurality of slits or apertures 104 is positioned over the adhesive layer 100.

In this embodiment, multiple slits 104 are arranged in columns instead of having a single slit extending in the vertical direction as shown in FIG. 5. The number of slits contained in each column can vary. In the embodiment illustrated in FIG. 7, for instance, each column contains either two slits or three slits. It should be understood, however, that in other embodiments a greater number of slits may be contained in each column.

As shown in FIG. 7, the slits 104 contained in one column are offset to the slits contained in an adjacent column. In other embodiments, however, all the slits may align together in rows that extend across the cover member 102.

The slits 104 in each column generally extend from about 10% to about 80% of the length of the cover member 102. For instance, each column can have a length that is about 50% to about 70% of the total length of the cover member and can comprise two or more slits.

With respect to the embodiment illustrated in FIG. 5 or the embodiment illustrated in FIG. 7, the actual lengths of the slits 104 can vary depending upon the particular application and various factors, including the location of the extensible member and the size of the extensible member. In one embodiment, for instance, the slits 104 can have a length of from about 3 mm to about 12 mm, such as from about 5 mm to about 10 mm. The spacing between the slits and the number of slits positioned along the extensible member can also vary depending upon the particular application. In general, for instance, the slits can be from about 3 mm to about 10 mm apart.

Figure 8:
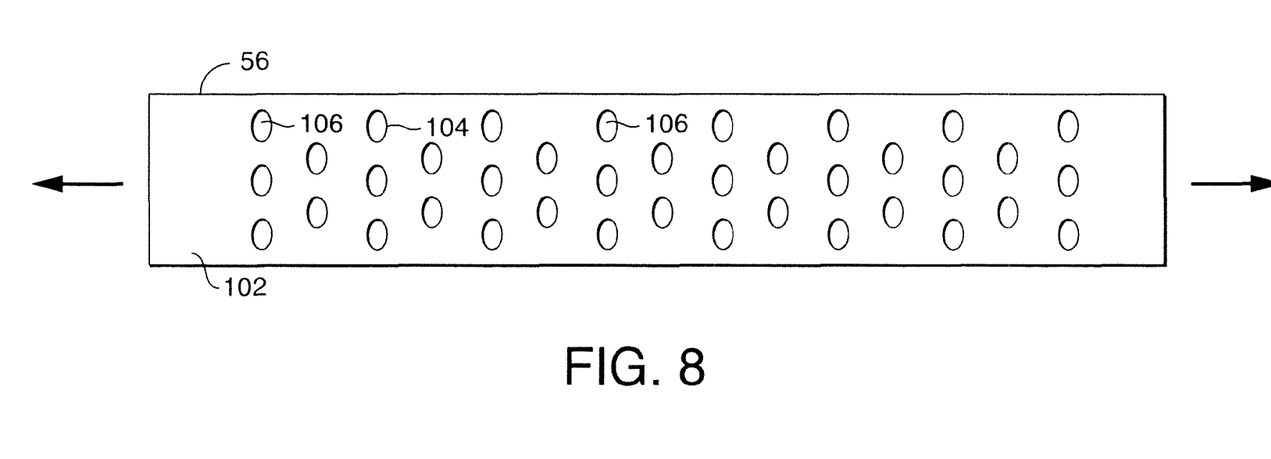
FIG. 8 is a plan view of the extensible adhesive member shown in FIG. 7 illustrated in a stretched condition.

As shown in FIGS. 6 and 8, as the elastic member 56 is stretched in the lateral direction, the slits 104 form openings 106. The openings 106 expose the adhesive layer 100 for allowing the adhesive to attach to a user's skin. The number of openings 106 formed into the cover member 102 when the elastic member is stretched and the size of the openings can be controlled so as to control the amount of adhesive that comes in contact with the user. In particular, depending upon where the extensible member is positioned on the garment, the size and number of openings can be designed so as to allow for attachment of the garment to the skin without creating any substantial discomfort. In fact, in one embodiment, the adhesive may actually improve the fit of the garment on the user.

In one embodiment, each of the openings 106 can expose a surface area of the adhesive layer of from about 0.1 square cm to about 0.6 square cm at 30 percent elongation. The total amount of surface area of the adhesive layer that is exposed by the openings 106 can also vary. For instance, the total surface area of the exposed adhesive layer is from about 5 to about 50 percent of the total surface area of the adhesive layer, such as from about 15 to about 35 percent at 30 percent elongation. When the extensible portion undergoes a 30 percent elongation, the apertures or slits form the openings that have a total surface area of from about 5 to about 100 $mm^2$.

As shown in FIGS. 5 and 7, the adhesive layer 100 can be directly applied to the outer surface of the elastic member 56. In other embodiments, however, the adhesive layer may be applied to any suitable extensible material that can then be attached to or placed over an elastic member. If the elastic member is directly incorporated into materials used to form the chassis of the garment, for instance, the adhesive member can be applied directly to the chassis or can be applied to an extensible material that is placed upon the chassis. For instance, if the liner of the absorbent article is made from an elastic material, the adhesive may be applied directly to the liner or can be applied to an extensible material that is later attached to the liner.

The adhesive layer 100 can be a continuous layer placed over the elastic member 56. Alternatively, the adhesive layer 100 can be discontinuous made from a plurality of discrete areas where the adhesive has been applied. For instance, in one embodiment, the adhesive layer may comprise discrete areas of adhesive that are placed directly below each of the slits 104.

In general, any suitable adhesive capable of securing the garment to one's skin without causing damage to the skin upon disengagement may be used in the present disclosure. Suitable adhesives may include hydrogels, silicones, acrylics, polyurethanes, polyesters, and polyamides. Other suitable adhesives include a rubber-based adhesive such as styrenebutadiene, polyisobutylene, polybutadiene and polyisoprene; a water soluble adhesive such as polyvinyl alcohol, polyvinyl acetate and methyl cellulose; and, desirably, a hot melt adhesive such as block copolymers of styrene-butadiene-styrene, styrene-isoprene-styrene, styrene-ethylenepropylene-styrene, styrene-ethylenebutylene-styrene and tetrablock copolymers such as styrene-ethylenepropylene-styrene-ethylenepropylene. Desirably, the adhesive is a pressure sensitive adhesive. The adhesive may also include other substances such as tackifying resins, oils and the like. Such adhesives are commercially available from Findley Adhesives Company, a business having offices in Wauwatosa, Wis. and the National Starch and Chemical Company, a business having offices located in Bridgewater, N.J.

In one embodiment, for instance, the adhesive may comprise a polysiloxane material. A pressure sensitive polysiloxane adhesive composition may generally be formed by curing a mixture of a lower alkenyl-functional polysiloxane, such as a vinyl containing polysiloxane, and a hydrogen containing polysiloxane copolymer containing active hydrogen groups. For example in one embodiment, the polysiloxane adhesive may comprise a two-part adhesive commercially available from the Dow Corning Corporation under the trade designation SYLGARD Q3-6636 silicone dielectric gel adhesive. In one embodiment, the polysiloxane adhesive can contain filler particles, such as fumed silica particles. The fumed silica particles can have a particle size of less than about 1 micron, such as from about 0.001 microns to about 0.05 microns.

In an alternative embodiment, an adhesive may be used that is based upon polyisobutylene. In many applications, it is desirable that the adhesive have a low adhesion to the skin such that it releases from the skin after a relatively short period of time. It has been discovered that suitable adhesives to provide such an improved fastenability are those which have the following properties.

As used herein, the term "shear storage modulus" refers to the shear storage modulus value determined according to the methods described in U.S. Pat. No. 6,277,106. The shear storage modulus value of an adhesive is meant to represent the flexibility or stretchability of the adhesive. In the different aspects, it is desired that the adhesive does not exhibit a shear storage modulus which is too low, since such will generally indicate that the adhesive lacks sufficient cohesive strength and will, thus, generally break apart and leave residue upon removal from a wearer's skin. Generally, adhesives which exhibit a higher shear storage modulus are desirable when the adhesive is configured to release from the skin after a short period of time. However, as the shear storage modulus of the adhesive increases, the flexibility of the adhesive will decline. Thus, an adhesive which exhibits a shear storage modulus which is too high may not conform to the wearer's body or may cause mechanical irritation.

Thus, to achieve a generally low level of adhesion to the wearer to provide the desired temporary securement, the adhesive can exhibit a shear storage modulus of at least about $1.0 \times 10^3$ and desirably at least about $7.8 \times 10^3$ dynes per square centimeter as measured at a temperature of about 20° C. and at a frequency of about 10 radians per second. For example, the adhesive may exhibit a shear storage modulus of from about $1.0 \times 10^3$ to about $6.0 \times 10^5$ and desirably from about $4.0 \times 10^4$ to about $6.0 \times 10^6$ dynes per square centimeter as measured at a temperature of about 20° C. and at a frequency of about 10 radians per second.

As used herein, the term "tan delta" refers to the tan delta value determined according to the methods described in U.S. Pat. No. 6,277,106. The tan delta value of an adhesive is meant to represent the ratio between the shear loss modulus and the shear storage modulus of the adhesive.

As used herein, the term "peel strength" refers to the peel strength of the adhesive as determined according to the Peel Strength Test described in U.S. Pat. No. 6,277,106. The peel strength of an adhesive is meant to represent the adhesive bond strength of the adhesive. In the different aspects, it is desired that the adhesive does not exhibit a peel strength which is too high, since such will generally indicate that the adhesive is too aggressive and will, thus, remain adhered to the skin of the wearer and cause pain and redmarking upon removal from the skin. Generally, adhesives which exhibit a lower peel strength are desirable when the adhesive is configured to release from the skin after a period of time. However, as the peel strength of the adhesive decreases, the adhesive may not adhere at all to the wearer's body.

Thus, to achieve the desired level of adhesion to the wearer to provide the desired temporary securement, the adhesive can exhibit a peel strength of no more than about 300 grams per centimeter of width, desirably no more than about 240 grams per centimeter of width, and more desirably no more than about 160 grams per centimeter of width of the adhesive pattern. For example, the adhesive 50 may exhibit a peel strength of from about 0 to about 240 grams per centimeter of width, desirably from about 10 to about 160 grams per centimeter of width, and more desirably from about 40 to about 100 grams per centimeter of width of the adhesive pattern.

The shear strength of an adhesive is another property of adhesives which is important to the selection of an appropriate adhesive for use in the present invention. The shear strength of an adhesive may vary as the duration of use extends. Accordingly, the shear strength of an adhesive can be determined at the time of application to provide an initial shear strength and at any later designated time to provide an aged shear strength. As used herein, the terms "initial shear strength" and "aged shear strength" refer to the shear strength of the adhesive as determined according to the Shear Strength Test described in U.S. Pat. No. 6,277,106.

The shear strength of an adhesive is also meant to represent the adhesive bond strength of the adhesive. In the different aspects, it is desired that the adhesive does not exhibit an initial shear strength which is too high, since such will generally indicate that the adhesive is too aggressive and will, thus, remain adhered to the skin of the wearer and cause pain and redmarking upon removal from the skin. Generally, adhesives which exhibit a lower initial shear strength are desirable when the adhesive is configured to release from the skin after a short period of time.

Thus, to achieve the desired level of adhesion to the wearer, the adhesive can exhibit an initial shear strength of no more than about 600 grams per square centimeter, desirably no more than about 530 grams per square centimeter, and more desirably no more than about 430 grams per square centimeter of the adhesive pattern. For example, the adhesive 50 may exhibit an initial shear strength of from about 0 to about 530 grams per square centimeter and desirably from about 30 to about 430 grams per square centimeter of the adhesive pattern.

The aged shear strength of an adhesive is meant to represent the shear strength of the adhesive after a specific period of time. Thus, the aged shear strength can indicate the likelihood of the adhesive to release from the skin after a short period of time. In the different aspects of the present invention, it is desired that the adhesive does not exhibit an aged shear strength which is too high, since such will generally indicate that the adhesive is too aggressive and will, thus, remain adhered to the skin of the wearer and cause pain and redmarking upon removal from the skin. Generally, adhesives which exhibit a lower aged shear strength are desirable when the adhesive is configured to release from the skin after a short period of time.

Thus, to achieve the desired level of adhesion to the wearer to provide the desired temporary securement of the garment about the wearer, the adhesive can exhibit an aged shear strength of no more than about 500 grams per square centimeter, desirably no more than about 450 grams per square centimeter, and more desirably no more than about 400 grams per square centimeter of the adhesive pattern. For example, the adhesive may exhibit an aged shear strength of from about 0 to about 400 grams per square centimeter, desirably from about 20 to about 340 grams per square centimeter, and more desirably from about 30 to about 250 grams per square centimeter of the adhesive pattern.

As described above, it is desirable that the adhesive of the different aspects of the present invention releases from the skin of the wearer after a period of time. Another property of an adhesive, the cyclic shear, can be used in the selection of an appropriate adhesive. As used herein, the term "cyclic shear" refers to the cyclic shear value of the adhesive as determined according to the Cyclic Shear Test described in U.S. Pat. No. 6,277,106.

In general, the cyclic shear of an adhesive represents the decreasing ability of an adhesive to remain adhered to the skin of a wearer as the wearer moves during use. The cyclic shear is a measure of the number of cycles of movement which an adhesive can endure before separating from a surface. In the different aspects, it is desired that the adhesive does not exhibit a cyclic shear which is too high, since such will generally indicate that the adhesive is too aggressive or too compliant and stretchable and will, thus, remain adhered to the skin of the wearer. Generally, adhesives which have a low cyclic shear, detach from the skin of the wearer after a relatively short duration.

Thus, the adhesive can exhibit a cyclic shear of no more than about 100 cycles and desirably no more than about 50 cycles as tested according to the Cyclic Shear Test. For example, the adhesive 50 may exhibit a cyclic shear of from 0 to about 100 cycles, desirably from 0 to about 50 cycles, and more desirably from 0 to about 20 cycles.

In a particular aspect, the adhesive exhibits a peel strength of no more than about 300 grams per centimeter of width, an initial shear strength of no more than about 600 grams per square centimeter, and a cyclic shear value of no more than about 100 cycles for improved performance.

The cover member 102 as shown in FIGS. 5-8 can also be made from various different materials. For instance, the cover member 102 can be made from a film, a nonwoven material, or a woven material. Additionally, the cover member 102 can also comprise a laminate made from multiple layers of materials. The cover member 102 should be easily extensible but need not be elastic. In one embodiment, the cover member 102 can be made from a neck bonded laminate. A necked cover provides for improved exposure of the adhesive layer 100 when the extensible member 56 is in a stretched state. The necked cover member also allows for a stiffer cover which also aids in the exposure of the adhesive layer 100.

In another embodiment, the cover member 102 is made from a meltblown web. Meltblown webs, for instance, are made from meltblown fibers. As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited on a collecting surface.

In an alternative embodiment, the cover member 102 can be made from a spunbond web. For instance, the spunbond web can be made from a polypropylene polymer.

The cover member 102 is generally secured over the adhesive layer 100. In one embodiment, for instance, the adhesive layer 100 can be used to secure the cover member 102 in place. In other embodiments, however, the cover member 102 may be further secured to the garment as desired. For instance, depending upon the material used to form the cover member, the cover member can be thermally bonded, ultrasonically bonded or connected to the garment through an adhesive in addition to the adhesive layer 100.

In the embodiments illustrated in the Figures, the adhesive member of the present disclosure is shown positioned over the back waist elastic member 56. It should be understood, however, that similar adhesive members may be positioned anywhere else on the garment as desired where an elastic portion exists. For instance, an adhesive member may also be positioned over the front waist elastic member 54 or over the containment flaps 46.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In accordance with the present disclosure, an adhesive member as described above may also be placed over the leg elastic members 58 to further enhance containment and prevent leakage of body fluids.

As described above, in addition to diapers as shown in the Figures, the teachings of the present disclosure may be applied to any suitable garment. For instance in other embodiments, adhesive members made according to the present disclosure may be applied to feminine hygiene products, adult incontinence products, hospital gowns, industrial wear, gloves, bandages, surgical drapes, and the like. For example, in one embodiment, adhesive members made according to the present disclosure may be incorporated over an elastic portion contained within a feminine hygiene product. For instance, in one embodiment, the adhesive members may be positioned over an elastic member on a feminine hygiene product that is positioned to contact the inner thigh of a wearer.

In still another embodiment, adhesive members made according to the present disclosure can be incorporated into an elastic cuff on a garment. The cuff, for instance, may be designed to surround the wrist or the leg of a wearer. The cuff, for instance, can be on a glove, a hospital gown, a protective industrial garment, or the like. The adhesive member of the present disclosure can be placed around the cuff over an elastic portion in order to provide a better seal so as to prevent the leakage of any fluids from the garment or alternatively to prevent contaminants present in the environment in which the garment is worn from getting into the garment.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A garment comprising:
a chassis having a shape configured to surround a portion of a wearer's body, the chassis including a front portion and a back portion and an inner surface that is placed adjacent to the wearer's body and an outer surface wherein the chassis defines at least a front inner surface and a back inner surface;
an extensible portion that permits the chassis to expand in an area for providing the chassis with a form fitting property around a portion of a wearer's body;
an adhesive member positioned on the back inner surface of the chassis and over the extensible portion, the adhesive member including an adhesive layer applied over the extensible portion and a cover member wherein the cover member is adjacent to the wearer's skin, the cover member substantially covering the adhesive layer and wherein, when the extensible portion is stretched in a lateral direction, the cover member defines openings facing the wearer's skin that expose the adhesive layer to the wearer's body; and wherein the adhesive layer of the adhesive member has low tack and a peel strength of no more than about 140 grams per centimeter of width and is configured to provide a cyclic shear value of no more than about 100 cycles, such that the adhesive will detach during use from the wearer's body after initial application.

2. A garment as defined in claim 1, wherein the garment comprises an absorbent article that includes an outer cover, an absorbent core, and a liner, the absorbent core being positioned between the outer cover and the liner, the liner defining the inner surface.

3. A garment as defined in claim 2, wherein the absorbent article, when positioned on a wearer's body, includes first and second leg openings and a waist opening, the extensible portion surrounding the waist opening.

4. A garment as defined in claim 2, wherein the absorbent article, when positioned on a wearer's body, includes first and second leg openings and a waist opening, the extensible portion is positioned around at least one of the leg openings.

5. A garment as defined in claim 2, wherein the absorbent article comprises a feminine care pad.

6. A garment as defined in claim 1, wherein the extensible portion comprises a cuff.

7. A garment as defined in claim 1, wherein the extensible portion comprises an elastic laminate.

8. A garment as defined in claim 7, wherein the elastic laminate comprises a stretch bonded laminate.

9. A garment as defined in claim 1, wherein the cover member comprises a nonwoven web.

10. A garment as defined in claim 1, wherein the cover member comprises a spunbond web.

11. A garment as defined in claim 1, wherein the cover member defines a plurality of apertures or slits that define the openings when the extensible portion is stretched.

12. A garment as defined in claim 11, wherein the cover member has a length that is generally parallel with the apertures or slits, the apertures or slits only extending over a portion of the length, the slits having a length from about 3 mm to about 12 mm.

13. A garment as defined in claim 12, wherein the apertures or slits are spaced apart a distance of from about 3 mm to about 10 mm.

14. A garment as defined in claim 11, wherein the apertures or slits have a length that is from about 20 percent to about 80 percent of the height of the cover member.

15. A garment as defined in claim 11, wherein, when the extensible portion undergoes a 30 percent elongation, the apertures or slits form the openings that have a total surface area of from about 5 to about 100 mm$^2$.

16. A garment as defined in claim 11, wherein the slits or apertures are arranged in columns over the cover member, each column containing a plurality of apertures or slits.

17. A garment as defined in claim 1, wherein the extensible portion comprises an elastic film upon which the adhesive layer is disposed.

18. A garment as defined in claim 1, wherein the adhesive layer of the adhesive member comprises a silicone, an acrylic, a polyurethane, a polyester, a polyamide, a styrene butadiene, a polyisobutylene, a polybuadiene, a polyisoprene, a polyvinyl alcohol, a polyvinyl acetate, a methyl cellulose, a styrene-butadiene-styrene, a styrene-isoprene-styrene, a styrene-ethylenepropylene-styrene, a styrene-ethylenepropylene-styrene-ethylenepropylene, a styrene-ethylene butylene-styrene, or mixtures thereof.

19. A garment as defined in claim 1, wherein the adhesive layer of the adhesive member defines a shear storage modulus of from about $1.0 \times 10^3$ to about $6.0 \times 10^6$ dynes per square centimeter as measured at a temperature of 20° C. and at a frequency of 10 radians per second.

20. A garment as defined in claim 1, wherein the adhesive layer of the adhesive member is configured to provide an initial shear strength of no more than about 600 grams per square centimeter.

21. A garment as defined in claim 1, wherein the adhesive layer of the adhesive member is configured to provide an aged shear strength of no more than about 500 grams per square centimeter.

22. A garment as defined in claim 1, wherein the adhesive layer comprises a plurality of discrete adhesive areas, the adhesive areas being position only beneath the openings defined by the cover member.

23. A garment as defined in claim 1, wherein the adhesive member is positioned on a flap positioned on the back inner surface of the chassis and over the extensible portion such that when the extensible portion is stretched in a lateral direction, the cover member on the flap defines openings facing the wearer's skin that expose the adhesive layer to the wearer's body.

* * * * *

UNITED STATES PATENT AND TRADEMARK OFFICE
CERTIFICATE OF CORRECTION

PATENT NO. : 8,226,624 B2  
APPLICATION NO. : 11/848594  
DATED : July 24, 2012  
INVENTOR(S) : Hancock-Cooke et al.

Page 1 of 1

It is certified that error appears in the above-identified patent and that said Letters Patent is hereby corrected as shown below:

On the Title Page, Item (56), Column 1, References Cited, the first reference "3,338,992..." should read --338,992...--

Signed and Sealed this  
Eighth Day of October, 2013

Teresa Stanek Rea  
*Deputy Director of the United States Patent and Trademark Office*